(12) United States Patent
Dardas et al.

(10) Patent No.: US 11,879,388 B2
(45) Date of Patent: Jan. 23, 2024

(54) SYSTEM AND METHOD FOR MONITORING FUEL ADDITIVES

(71) Applicant: Raytheon Technologies Corporation, Farmington, CT (US)

(72) Inventors: Zissis A Dardas, Worcester, MA (US); Haralambos Cordatos, Colchester, CT (US); Ying She, Rocky Hill, CT (US)

(73) Assignee: RTX Corporation, Farmington, CT (US)

( * ) Notice: Subject to any disclaimer, the term of this patent is extended or adjusted under 35 U.S.C. 154(b) by 37 days.

(21) Appl. No.: 17/521,024

(22) Filed: Nov. 8, 2021

(65) Prior Publication Data

US 2022/0056841 A1    Feb. 24, 2022

Related U.S. Application Data

(62) Division of application No. 16/193,146, filed on Nov. 16, 2018, now Pat. No. 11,193,420.

(51) Int. Cl.
| | | |
|---|---|---|
| F02C 3/30 | (2006.01) | |
| F02C 7/22 | (2006.01) | |
| F02C 7/232 | (2006.01) | |
| F02C 9/26 | (2006.01) | |
| F02C 9/40 | (2006.01) | |
| F02M 25/00 | (2006.01) | |

(52) U.S. Cl.
CPC ............... *F02C 3/30* (2013.01); *F02C 7/22* (2013.01); *F02C 7/232* (2013.01); *F02C 9/263* (2013.01); *F02C 9/40* (2013.01); *F02M 25/00* (2013.01)

(58) Field of Classification Search
CPC .... F02C 9/263; F02C 9/40; F02C 7/22; F02C 7/232; F02C 7/236; F02C 3/30
See application file for complete search history.

(56) References Cited

U.S. PATENT DOCUMENTS

| 4,346,689 A | 8/1982 | Neely |
| 6,315,815 B1 | 11/2001 | Spadaccini et al. |
| 6,609,534 B1 | 8/2003 | Beaney et al. |
(Continued)

FOREIGN PATENT DOCUMENTS

| CN | 1107935 A | * | 9/1995 | |
| KR | 101376464 B1 | | 3/2014 | |
| WO | WO-2007080070 A1 | * | 7/2007 | ............... C10L 1/305 |

OTHER PUBLICATIONS

European search report for patent application No. 19166494.5 dated Aug. 19, 2019.

(Continued)

*Primary Examiner* — William H Rodriguez
(74) *Attorney, Agent, or Firm* — Bachman & LaPointe, P.C.

(57) ABSTRACT

A system for monitoring fuel additives on board a vehicle includes a fuel line carrying fuel from a fuel source to an engine; a fuel additive sensor configured to measure concentration of additives in fuel at a point along the fuel line; a fuel additive dispenser connected in parallel to the fuel line; at least one flow control device for controlling an amount of flow from the fuel line into the fuel additive dispenser; and a controller configured to receive input from the fuel additive sensor and to control the flow control device to adjust the amount of the flow from the fuel line into the fuel additive dispenser.

7 Claims, 6 Drawing Sheets

(56) References Cited

U.S. PATENT DOCUMENTS

| | | | |
|---|---|---|---|
| 6,623,636 B2 * | 9/2003 | Rohrbach | B01D 37/025 |
| | | | 210/287 |
| 6,709,492 B1 | 3/2004 | Spadaccini et al. | |
| 6,835,218 B1 | 12/2004 | Drozd et al. | |
| 6,877,488 B2 * | 4/2005 | Washeleski | F02M 25/08 |
| | | | 123/41.31 |
| 7,055,505 B2 * | 6/2006 | Washeleski | F02D 41/0032 |
| | | | 123/519 |
| 7,159,741 B2 | 1/2007 | Dehn et al. | |
| 7,393,388 B2 | 7/2008 | Spadaccini et al. | |
| 7,431,818 B2 | 10/2008 | Cipollini | |
| 7,744,827 B2 | 6/2010 | Vanderspurt et al. | |
| 7,950,216 B2 | 5/2011 | Dooley et al. | |
| 8,153,549 B2 * | 4/2012 | Cho | B01J 37/0244 |
| | | | 502/527.12 |
| 8,210,826 B2 | 7/2012 | Freeman | |
| 8,702,995 B2 | 4/2014 | Kelly et al. | |
| 9,103,261 B1 | 8/2015 | White et al. | |
| 9,267,465 B2 | 2/2016 | Monsallier et al. | |
| 9,856,788 B2 | 1/2018 | Guinther | |
| 11,193,420 B2 * | 12/2021 | Dardas | F02C 9/263 |
| 2004/0026291 A1 | 2/2004 | Drozd et al. | |
| 2007/0240649 A1 | 10/2007 | Freeman | |
| 2010/0228400 A1 | 9/2010 | Johnson et al. | |
| 2010/0242490 A1 | 9/2010 | Symonds | |
| 2017/0368504 A1 | 12/2017 | Hamad et al. | |
| 2018/0363552 A1 * | 12/2018 | Zhang | F02C 3/24 |
| 2019/0301368 A1 * | 10/2019 | Dardas | B64D 37/34 |

OTHER PUBLICATIONS

European search report for patent application No. 19 20 9847 dated Jun. 12, 2020.

U.S. Non-final office action for U.S. Appl. No. 15/942,982 dated Dec. 5, 2019.

European search report for patent application No. 21 20 5522.2 dated Nov. 11, 2021.

* cited by examiner

SYSTEM AND METHOD FOR MONITORING FUEL ADDITIVES

CROSS REFERENCE TO RELATED APPLICATIONS

This application is a divisional application of U.S. application Ser. No. 16/931,146 filed Nov. 16, 2018.

BACKGROUND

The present disclosure relates to on-board delivery of fuel additives, and more particularly, system and method for on-board or in situ monitoring of fuel additives.

Fuel additives are frequently needed for various types of fuel including vehicular fuel, especially aircraft fuel, and the like. These fuel additives can be essential for fuel stabilization, and numerous other functions with respect to fuel and desirable combustion and related properties.

For example, fuel stabilization will be required on next generation aircraft in order to meet performance and operability targets. Increased thermal loads and decreased fuel flows necessitate higher temperature fuel. The most viable fuel stabilization technologies require removal of dissolved oxygen, which is the root cause of carbonaceous deposits.

As an alternative to dissolved oxygen removal, additive packages have been developed which allow for an increase in fuel temperature up to certain limits. For example, one package allows an increase in operating fuel temperature of up to 100° F. This additive package was designed for injection into JP-8 fuel at refueling truck loading racks. There is a move to eliminate the use of JP-8 at military installations, replacing it with Jet-A fuel, with the additives injected while the fuel is in the logistics pipeline.

With responsibility for additive incorporation in the fuel shifted away from refiners and toward separate commercial entities, it is now possible that an aircraft, especially if operating outside the USA, may receive fuel that contains a lower concentration of the required additives than the specifications require. This creates the need to validate the presence and the correct concentration of additives in the fuel tank.

SUMMARY

In one non-limiting configuration, a system is provided for monitoring fuel additives on board a vehicle comprising; a fuel line carrying fuel from a fuel source to an engine; a fuel additive sensor configured to measure concentration of additives in fuel at a point along the fuel line; a fuel additive dispenser connected in parallel to the fuel line; at least one flow control device for controlling an amount of flow from the fuel line into the fuel additive dispenser; and a controller configured to receive input from the fuel additive sensor and to control the flow control device to adjust the amount of the flow from the fuel line into the fuel additive dispenser.

In one non-limiting configuration, the fuel additive dispenser is positioned along a fuel additive bypass line connected at an upstream end to the flow control device and connected at a downstream end back to the fuel line.

In another non-limiting configuration, the fuel additive sensor is positioned upstream of or at the flow control device.

In a further configuration, the fuel additive sensor is positioned downstream of the downstream end of the fuel additive bypass line.

In a still further configuration, the controller is configured to compare the concentration with a pre-set additive requirement specification, and to control the flow control device to increase flow through to fuel additive dispenser when the concentration is less than the specification.

In another non-limiting configuration, the fuel additive dispenser contains a plurality of fuel additives and wherein the controller is configured to increase flow through the fuel additive dispenser when the concentration of any one or more of the plurality of fuel additives is less than the specification.

In still another non-limiting configuration, the fuel additive dispenser is a passive fuel additive dosing system.

In a further non-limiting configuration, the passive fuel additive dosing system comprises a cartridge; a membrane-based contractor within the cartridge; a fuel inlet to the cartridge connected to receive diverted flow from the flow control device; a fuel outlet from the cartridge connected to return flow back to the fuel line; and an additive within the membrane-based contractor, the membrane-based contractor being arranged in the cartridge such that, with fuel in the cartridge, a fuel contact area with the membrane-based contractor is dependent on a fuel flow rate to passively dispense a proportional amount of the additive in to the fuel.

In another non-limiting configuration, the fuel line, the fuel additive sensor, the fuel additive dispenser and the at least one flow control device are within a fuel tank of a vehicle.

In another non-limiting configuration, the vehicle is an aircraft.

Another non-limiting configuration relates to a method for monitoring fuel additives on board a vehicle, comprising: flowing fuel from a fuel tank along a fuel line to an engine; sensing concentration of additives in the fuel at a point along the fuel line; determining whether the concentration of the additive in the fuel is less than a fuel additive specification; when the concentration is less than the specification, operating a flow control device to divert a portion of the fuel from the fuel line along a parallel line to a fuel additive dispenser.

The foregoing features and elements may be combined in various combinations without exclusivity, unless expressly indicated otherwise. These features and elements as well as the operation thereof will become more apparent in light of the following description and the accompanying drawings. It should be appreciated that however the following description and drawings are intended to be exemplary in nature and non-limiting.

BRIEF DESCRIPTION OF THE DRAWINGS

Various features will become apparent to those skilled in the art from the following detailed description of the disclosed non-limiting embodiment. The drawings that accompany the detailed description can be briefly described as follows.

DETAILED DESCRIPTION

The disclosure relates to a system and method for onboard or in situ monitoring of fuel additives in fuel being supplied to an engine of a vehicle, for example an aircraft. The presently disclosed system and method operate in conjunction with a fuel additive dispenser such as, but not limited to, the dispenser disclosed in U.S. patent application Ser. No. 15/942,982, filed Apr. 2, 2018, which is incorporated herein in its entirety by reference. The present disclosure operates in conjunction with such a dispenser to monitor concentration of fuel additives in a fuel tank, and to ensure the proper level of fuel additives in the fuel as it is fed from the fuel tank to the engine of the vehicle or aircraft. The system and method thereby ensure proper additive levels in an environment wherein fuels intended to be provided with certain levels of additives are provided under circumstances which are not as regulated as may be desired.

Figure 1:
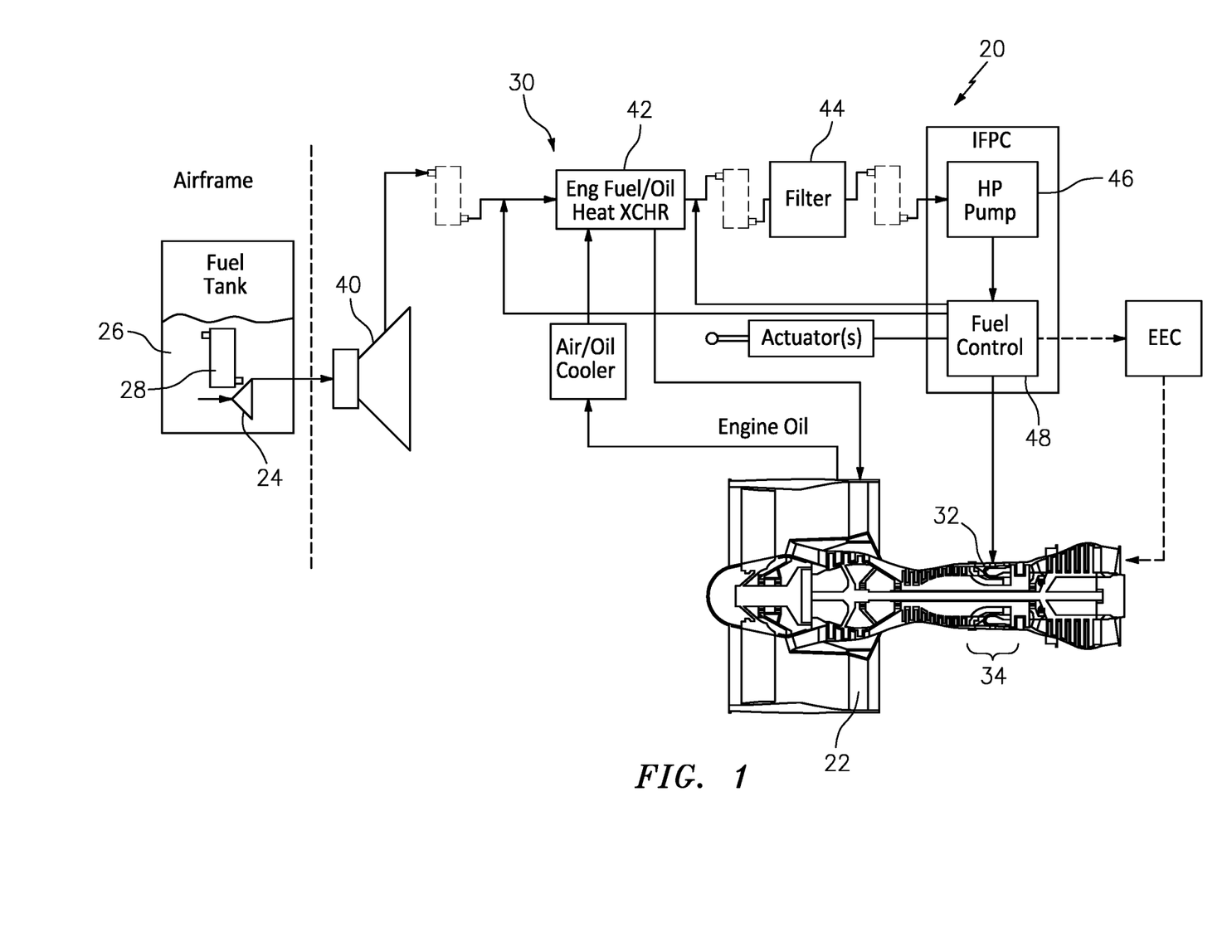
FIG. 1 is a schematic cross-section of a fuel system for a gas turbine engine.

FIG. 1 schematically illustrates a fuel system 20 for an engine 22. The engine 22 may be, for example but not limited to, a gas turbine engine utilized for propulsion of an aircraft, a gas turbine engine utilized as an auxiliary power unit (APU) or other system. To ensure that the increased heat sink capability is enabled by fuel additives, control of the additive blending operation is performed on-board the vehicle as opposed to relying on ground operations. This also avoids interference with coalescing filters, etc.

The fuel system 20 may generally include a tank pump 24 to supply fuel from a fuel tank 26 through a passive fuel additives dosing system 28 to a fuel subsystem 30, thence to a fuel manifold 32 in a combustor section 34 of the engine 22. The fuel subsystem 30, in one example, may include a boost pump 40, an engine fuel-oil heat exchanger 42, a filter system 44, a high-pressure fuel pump 46 and control system 48. The fuel subsystem 30 may alternatively or additionally include various components such as multiple fuel tanks, air-oil coolers, fuel driven actuators fuel modules, solenoid valves, metering valves, shut-off valves, spill valves, and other filters. It should be appreciated that various other systems, subsystems and components may alternatively or additionally be provided and are contemplated as included by the fuel subsystem 30. Although the passive fuel additives dosing system 28 will be described primarily as within the low pressure fuel tank 26, the passive fuel additives dosing system 28 may be directly associated with the fuel tank 26 and/or distributed elsewhere in the fuel system 20 such as downstream of the boost pump 40 and upstream of the engine fuel-oil heat exchanger 42; downstream of the engine fuel-oil heat exchanger 42 and upstream of the filter system 44; and/or downstream of the filter system 44 and upstream of the high pressure fuel pump 46.

Figure 2:
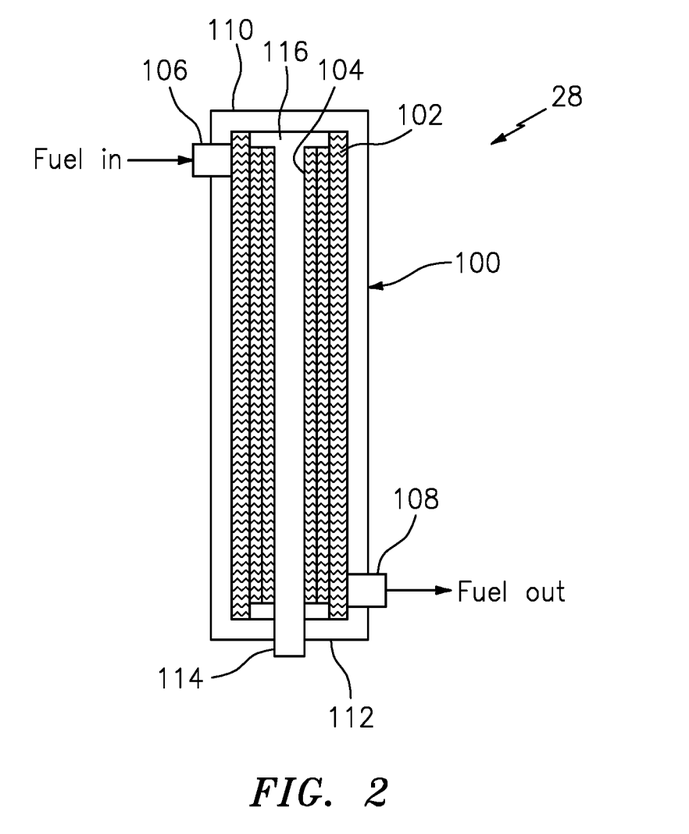
FIG. 2 is an enlarged sectional view of a fuel additives dosing system.

With reference to FIG. 2, the passive fuel additives dosing system 28 generally includes a cartridge 100, a membrane-based contactor 102 within the cartridge 100, and an additive 104 within the membrane-based contactor 102. The cartridge 100 includes a fuel inlet 106 and a fuel outlet 108 for communication with the fuel subsystem 30.

The membrane-based contactor 102 is arranged within the cartridge 100 such that, with fuel in the cartridge 100, a fuel contact area with the membrane-based contactor 102 is dependent on a fuel flow rate to passively dispense a proportional amount of the additive 104 into the fuel.

In one embodiment, the membrane-based contactor 102 is sized and oriented within the cartridge 100 to facilitate metering of the fuel contact area with the membrane-based contactor 102 in relation to the fuel flow rate to passively dispense the additive 104. In another embodiment, the fuel outlet 108 is arranged with respect to the fuel inlet 106 to facilitate metering of the fuel contact area. The fuel inlet 106 can be located adjacent a top 110 of the cartridge 100 and the fuel outlet 108 adjacent to a bottom 112 of the cartridge 100. This facilitates draining of the membrane-based contactor 102 once fuel flow has stopped such that osmotic pressure will not continue to drive additives into the fuel which may otherwise result in large concentrations of additives in the remaining volume of fuel. It should be appreciated that relative positional terms such as "top" and "bottom" are with respect to a normal operational attitude of the vehicle such as level flight.

The membrane-based contactor 102 may include a non-porous or a porous membrane. A non-porous membrane may be a reverse selective membrane to permeate large molecules over smaller ones, based on differences in solubility rather than diffusivity. Suitable membranes include silicone rubbers, poly-methyl pentyl, and poly-trimethyl-silyl-propyl, and other such reverse selective types. Typical polymer non-porous membranes would be unsuitable for this application as membranes such as those typically used for aircraft fuel tank inerting (based on polyimides, polysulfones or polycarbonates) would result in very low permeance of the large molecules comprising the fuel additives package as well as membranes such as those used for fuel stabilization, which are inherently oleophobic (fuel and oil repellent).

A porous membrane may comprise an oleophobic layer overcoating the outer diameter of a nanoporous polymer film to provide a barrier that facilitates prevention of the fuel from entering into the bore of each hollow fiber while the additives can exit therefrom. In one example, the porous membrane may have a thickness between about 50 nanometers and about 4 microns with pores of an average pore diameter less than or equal to 0.06 microns.

Figure 3:
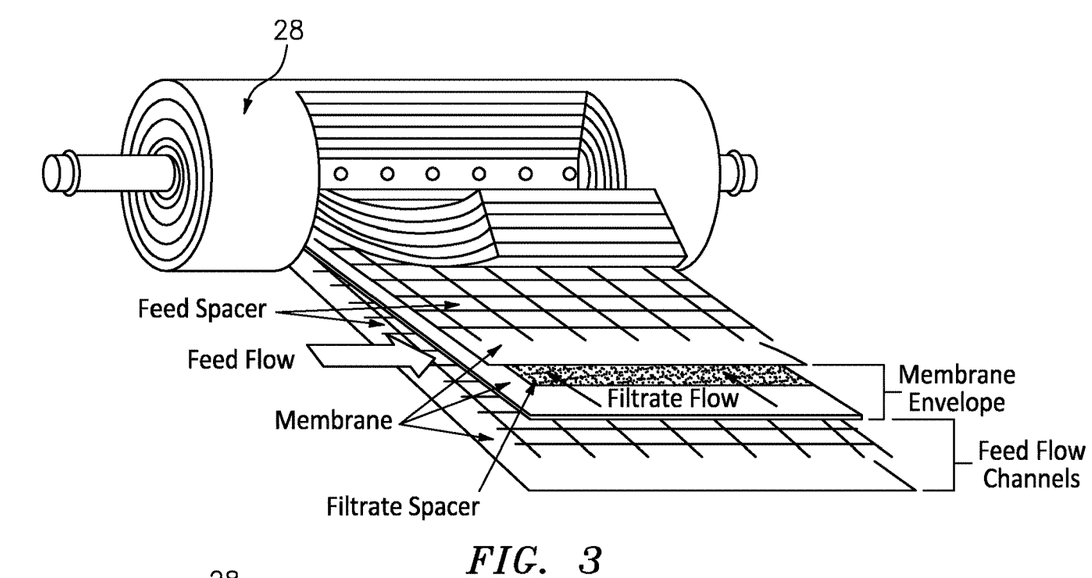
FIG. 3 is a membrane-based contactor for the fuel additives dosing system according to an alternative embodiment.
Figure 4:
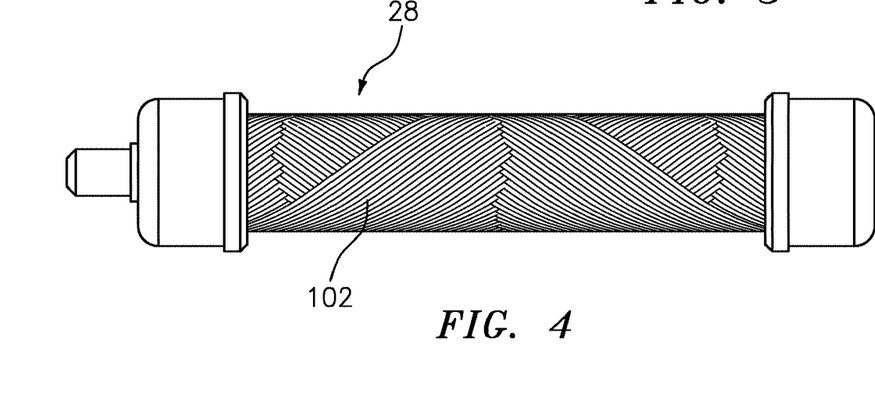
FIG. 4 is a membrane-based contactor for the fuel additives dosing system according to an alternative embodiment.
Figure 5:
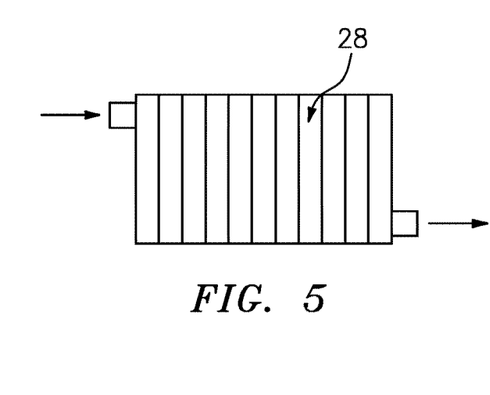
FIG. 5 is a membrane-based contactor for the fuel additives dosing system according to an alternative embodiment.

The membrane-based contactor 102 may be formed as a bundle of hollow fibers, in which a bore of each fiber contains the additive in a solution, suspension, or emulsion form. The relatively large surface area afforded by hollow fibers facilitates effective release of the additive when the flow rate is high. The outside surface of each hollow fiber of the bundle of hollow fibers is wetted by the fuel that enters the cartridge 100 from the fuel inlet 106 and exits from the fuel outlet 108. Each hollow fiber may include a porous support and a non-porous or porous membrane on an outer diameter of the porous support. Other forms of the membrane-based contactor 102 may be a spiral-wound configuration (FIG. 3), a hollow-fiber bundle (FIG. 4), or plate-and-frame configuration (FIG. 5). For the porous membrane, examples include both organic (polymeric) and inorganic (e.g. ceramic) membranes.

The additive can include anti-oxidants such as hindered phenols, metal deactivators, and dispersants that diffuse across the membrane-based contactor 102 due to the difference in osmotic pressure inside and outside of the hollow fibers. Depending on the application, some or all of the additive can be added as a concentrated liquid that is diluted to meet the specified application. The driving force for the additive to permeate the membrane-based contactor 102 is a concentration gradient (higher in the bore, lower in the fuel). Since the hollow fibers are always filled with the additive, the concentration difference between the inside (exposed to the additive) and the outside (exposed to flowing fuel) is essentially constant. Therefore, overall mass transfer is determined by the amount of membrane surface area wetted by the flowing fuel. This, in turn, is determined by the fuel flow rate and a recommended additive dosage, for example, 100 mg/L.

Figure 6:
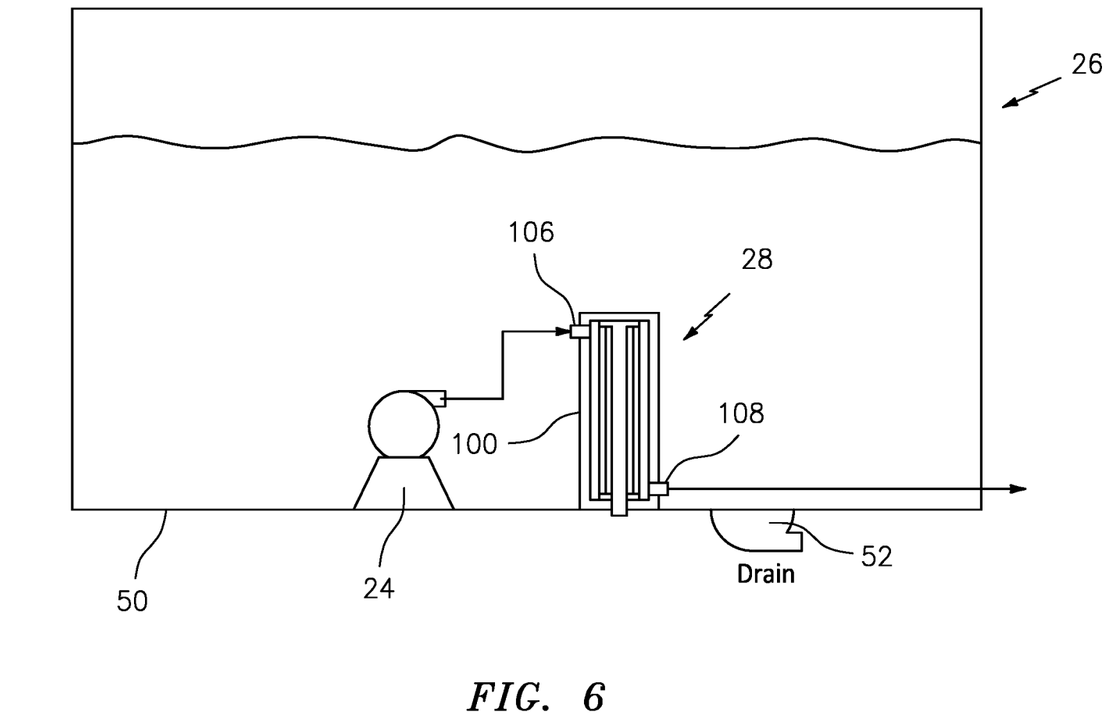
FIG. 6 is an enlarged sectional view of a fuel tank with a fuel additives dosing system.

The cartridge 100, in one embodiment, is located at a bottom 50 of the fuel tank 26 with the fuel outlet 108 adjacent to a tank fuel drain 52 in the fuel tank 26 to facilitate draining of fuel from the cartridge 100 (FIG. 6). An additive inlet 114 (FIG. 2) for refilling the additive is located at the bottom 112 of the cartridge 100. The additive inlet 114 communicates with a manifold 116 adjacent to the top 110 of the cartridge 100. The manifold 116 supplies additive by gravity such that the hollow fibers are always filled with the additive. Replenishment of the manifold 116 may occur over various intervals and may be conveniently performed at regular intervals as typical operators drain fuel tanks daily to avoid accumulation of water in the fuel tank. Alternatively, the entire cartridge 100 may be replaceable.

Figure 7:
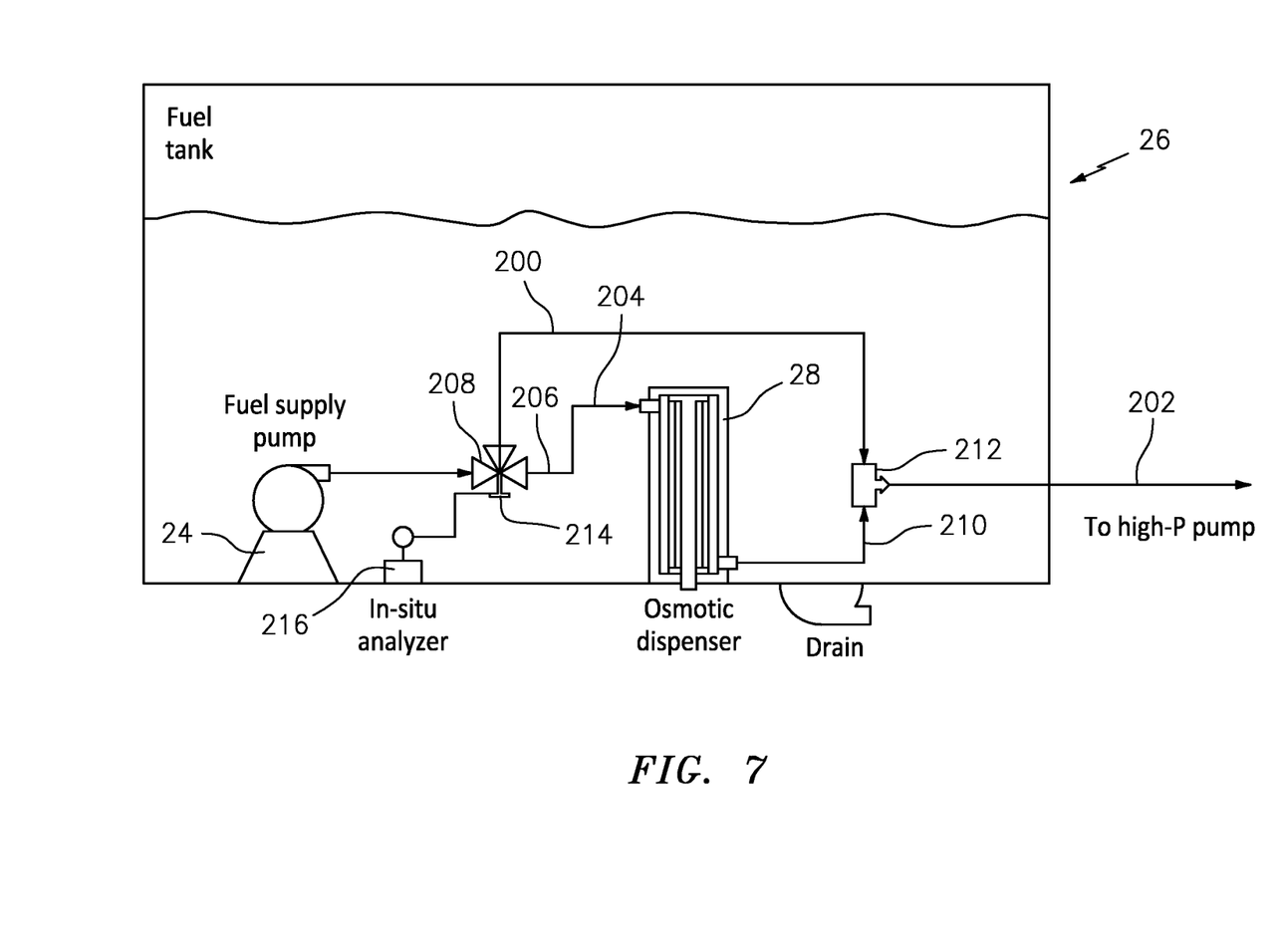
FIG. 7 shows a system for monitoring fuel additive concentration.

FIG. 7 shows a flow scheme or layout according to one non-limiting aspect of the present disclosure. In this system, a fuel tank 26 is shown containing a fuel additive dispenser such as fuel additives dosing system 28. Within fuel tank 26, a fuel supply pump 24 pumps fuel along a fuel line 200 to a high pressure pump which is schematically illustrated by arrow 202 exiting tank 26. Dispenser 28 is positioned along a parallel line 204, in parallel with line 200, and connected at an upstream end 206 by way of a flow control device such as a three way valve 208. The bypass line 204 is connected at a downstream end 210 back to the main fuel line 200, for example through a junction 212. A sensor 214 is positioned along fuel line 200, and is communicated with a controller 216 such that measurements taken by sensor 214 can be analyzed to determine whether fuel in fuel line 200 contains sufficient fuel additives. Controller 216 is configured to issue controlling commands to alter the position of flow control device 208 and control how much flow of fuel is passed through the main fuel line 200, and how much fuel is diverted through bypass line 204 into dispenser 28. Controller 216 is configured to compare levels of additives within the fuel, particularly to determine whether the additives are present in at least a specification amount of additive.

In the configuration of FIG. 7, sensor 214 and controller 216 quantify the additive concentration in the fuel tank and adjust the amount of flow through dispenser 28. If the concentration of additive is too low, controller 216 will operate flow control device 208 to increase the amount of flow of fuel through dispenser 28 such that the combined fuel, downstream of junction 212, will have a higher additive concentration that is closer to the specified value. In this way, fuel is monitored onboard, between the fuel tank and engine, to ensure that the fuel has proper additives to address the various needs of a particular fuel.

Sensor 214 can be any of numerous different types of available sensors which can be in the form of a mass spectrometer (mass spec), which are available on a chip. These small-scale devices, such as an Ion Mobility Spectrometry (IMS sensor by Owlstone Technology), can produce an ultra-fast chemical separation and detection which exploits the unique properties of ionized products of the chemical sample, utilizing the unique spectral fingerprint of various different chemicals. This produces a very fast and accurate analysis of contents of the fuel.

Chip-based mass spectrometers are particularly well suited to the present system and method since they can be implemented in compact configurations, with very low power requirements. Other types of sensors could be utilized within the scope of the present disclosure. However, one particularly well suited configuration of sensor is a sensor based upon Ion Mobility Spectrometry for the reasons set forth above.

Sensor 214 is connected to controller 216 for example, as schematically illustrated in FIG. 7, to pass the data collected by sensor 214 to controller 216, where this data is analyzed. Controller 216 preferably stores or has access to a stored profile of fuel, including a specification of which fuel additives should be present, and in what quantities. With access to this information, controller 216 can rapidly determine whether there is any deficiency in one or more additives which is intended to be present in the fuel. In this regard, additives within dispenser 28 would be selected to correspond to the additives which are desired in a particular fuel profile or specification. Thus, controller 216 can be configured to issue commands to flow control device 208 to pass additional fuel through dispenser 28 under circumstances where one or more additives is not present in the desired concentration. Further, controller 216 can be configured to determine a magnitude of shortage of the fuel additive, and to divert a proportionally increased amount of flow of fuel to dispenser 28 depending upon the magnitude of shortage of the additive.

Flow control device 208 can be any suitable three-way valve which accepts input from one source, such as fuel supply pump 24, and which has a controllable structure of configuration to allocate flow between two different branches, in this case fuel line 200 and bypass line 204. Junction 212 can be any suitable flow control structure to combine flows from fuel line 200 and bypass line 204, preferably with a minimum of flow resistance or the like.

Figure 8:
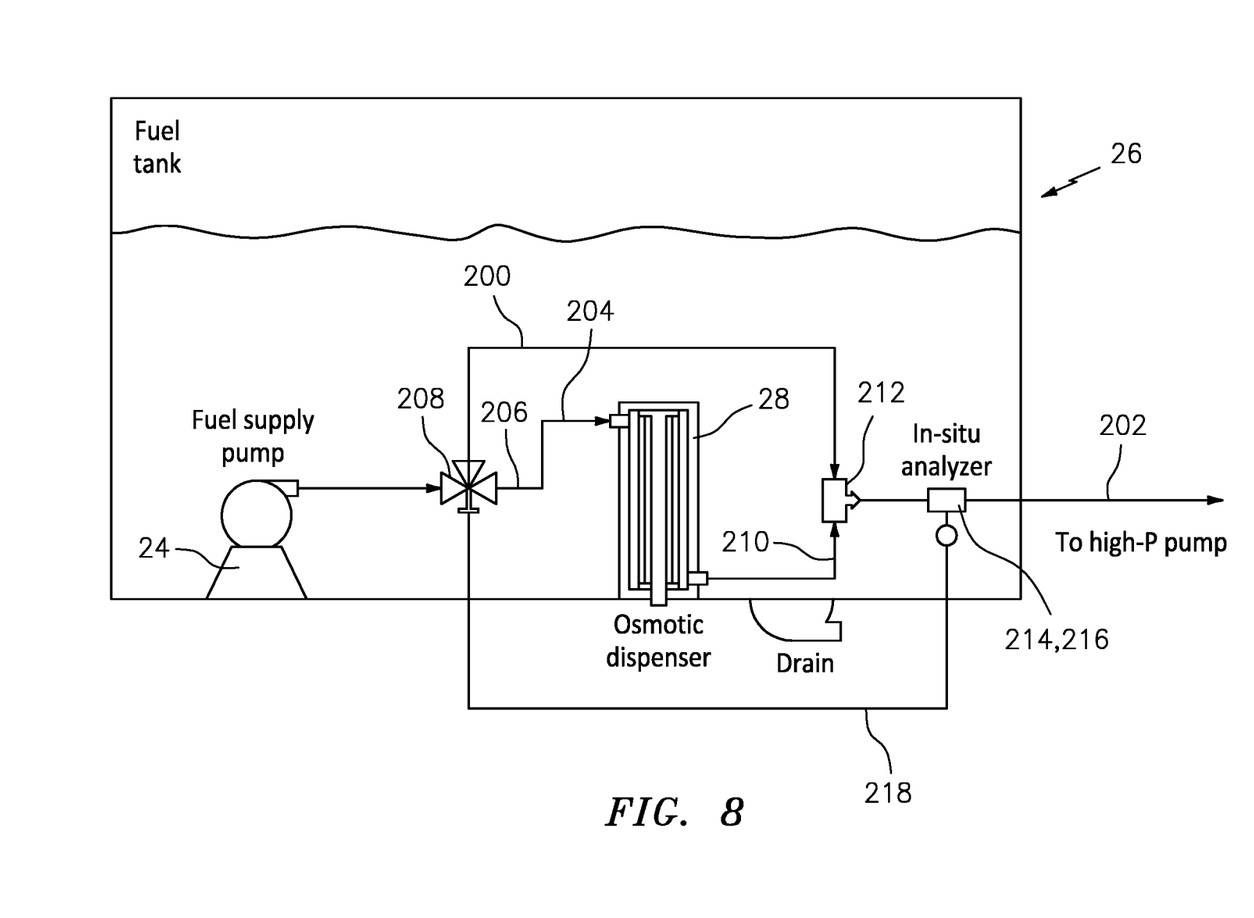
FIG. 8 shows an alternative system for monitoring fuel additive concentration.

FIG. 8 shows an alternative configuration of the system according to the present disclosure, wherein sensor 214 is positioned at a point along fuel line 200 which is downstream of the additive dispenser 28. In this configuration, sensor 214 and controller 216 which, in this example, is integrated with sensor 214, checks fuel for presence of proper additives, and then sends commands (illustrated schematically by line 218) to flow control device 208 to control the flow of fuel, and the amount of fuel which flows to dispenser 28, in similar fashion to that which is discussed above. In the configuration in FIG. 8, however, fuel additive level of fuel as it is supplied to the high pressure pump is directly measured, which can be seen as advantageous for purposes of ensuring that adjustments are made and then confirmed to produce the desired level of additive.

Considering FIGS. 7 and 8 together, a further non-limiting configuration could involve utilization of two sensors, with one sensor being in the position shown in FIG. 7 and the second sensor being shown in FIG. 8. In this way, the flow control device could be controlled primarily based upon input from the first sensor and additive content at the upstream side, and then the changes made could be confirmed by the downstream sensor or further adjustments made, if necessary, due to levels of an additive still not being reached.

Thus, according to the various configurations presently disclosed, fuel additive sensor 214 can be positioned upstream of or at flow control device 208, or could be positioned downstream of the downstream end 210 of the fuel additive bypass line 204, or sensors could be positioned in both of these locations.

It should also be appreciated that particular specifications for a fuel may require the presence of a number of different additives, and sensors 214 with controller 216 can be configured to check for the presence of each of these additives. Furthermore, controller 216 is programmed to increase fuel flow through dispenser 28 if any one of the plurality of fuel additives is not present in the desired concentration.

It should be appreciated that the system and method of the present disclosure could be implemented for a single fuel specification determined globally for an entire operation. Alternatively, it may be desirable to allow further configuration of controller 216 to control which additives are being monitored. For example, a fuel to be used in a very cold climate could require a different additive package than a fuel to be utilized in a very hot climate. Thus, it may be desirable in one configuration to allow controller 216 to be configured by an operator to correspond to a particular fuel additive specification.

Furthermore, it should be appreciated that while dispenser 28 in the present disclosure contains a combination of additives which are all dispensed into a fuel together, it is well within the scope of the present disclosure that a dispenser 28 would be operative to individually dispense different additives, and multiple dispensers or internal dispenser flow passages could be configured such that sensor 214 and controller 216 would increase flow through that portion of a dispenser 28 which would increase concentration of only one additive out of an additive package. This would conceivably lead to much more complex flow structures, and it may be that it would be preferable to simply increase the concentration of all additives within a tolerable range such that the level of one additive could be raised. Nevertheless, it is within the scope of the present disclosure to individually control specific additives of an entire additive package.

The system of the present disclosure functions as follows.

During operation fuel from tank 26 is pumped, for example by pump 24, from the fuel tank along a fuel line 200 and ultimately to an engine of the vehicle. In FIGS. 7 and 8, the portion of this path is shown concluding in line 202 which leads to a high –p pump. The remainder of a possible flow path is shown, for example in FIG. 1.

While such fuel is flowing, concentration of additives in the fuel is sensed, for example with sensor 214 in any of the disclosed positions. Data from the sensor is passed to a controller, which analyzes the data and compares to a profile of additives in a desired fuel specification. During normal operation, it is anticipated that fuel flow would be entirely through the main fuel line 200 as illustrated in FIGS. 7 and 8. This would be indicative of the fuel having been supplied to the aircraft or other type of vehicle with the proper level of additives in the fuel. If the controller determines that the concentration of additive in the fuel line is less than a fuel additive specification, commands are then sent to the flow control device to divert some flow of fuel from the main fuel line into the bypass fuel line and through the dispenser of additives. The amount of fuel diverted can be adjusted, depending upon the capability of the flow control device in question. Assuming that the flow control device can be controlled to variably select the amount of fuel which is diverted toward the dispenser, than the amount of fuel to be diverted may be proportional to the shortage of additive which is detected by the sensor and controller. Fuel diverted through the dispenser has additional additives dispensed into same, and is then rejoined to the main flow downstream of the dispenser. The combined flow then has a higher additive concentration.

In configurations such as that shown in FIG. 8, when a sensor is positioned downstream of the fuel additive device, measurements can advantageously be taken of the fuel additive concentration in fuel being supplied out of fuel tank 26, and thereby the adjustments can be insured to be producing the desired resultant fuel additive concentration.

Applications for fuel stabilization include kerosene-based fuels for aviation and diesel fuel stabilization for transportation (including terrestrial and marine), heavy equipment, and power generation. The passive fuel additives dosing system 28 is a relatively uncomplicated, passive osmotic dispenser device that leverages osmotic pressure, as opposed to a power source with dosing properties tuned by the characteristics of the membrane-based contactor 102 as opposed to complex control systems.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be appreciated that steps may be performed in any order, separated or combined unless otherwise indicated and will still benefit from the present disclosure.

The foregoing description is exemplary rather than defined by the limitations within. Various non-limiting embodiments are disclosed herein, however, one of ordinary skill in the art would recognize that various modifications and variations in light of the above teachings will fall within the scope of the appended claims. It is therefore to be appreciated that within the scope of the appended claims, the disclosure may be practiced other than as specifically described. For that reason the appended claims should be studied to determine true scope and content.

What is claimed is:

1. A method for monitoring fuel additives on board a vehicle, comprising:
   flowing fuel from a fuel tank along a fuel line to an engine;
   sensing concentration of additives in the fuel at a point along the fuel line;
   comparing the concentration of the additive in the fuel to a fuel additive specification;
   determining that the concentration is less than the specification;
   operating a flow control device to divert a portion of the fuel from the fuel line along a parallel line to a fuel additive dispenser and back to the fuel line;
   determining that the concentration meets the specification; and
   operating the flow control device to bypass the fuel additive dispenser, wherein the fuel additive dispenser is a passive fuel additive dosing system which comprises a cartridge; a membrane-based contactor within the cartridge; a fuel inlet to the cartridge connected to receive diverted flow from the flow control device; a fuel outlet from the cartridge connected to return flow back to the fuel line; and an additive within the membrane-based contactor, the membrane-based contactor being arranged in the cartridge such that, with fuel in the cartridge, a fuel contact area with the membrane-based contactor is dependent on a fuel flow rate to passively dispense a proportional amount of the additive into the fuel.

2. The method of claim 1, wherein the fuel additive dispenser is positioned along a fuel additive bypass line connected at an upstream end to the flow control device and connected at a downstream end back to the fuel line.

3. The method of claim 2, wherein the sensing step is carried out with a fuel additive sensor positioned upstream of or at the flow control device.

4. The method of claim 2, wherein the sensing step is carried out with a fuel additive sensor positioned downstream of the downstream end of the fuel additive bypass line.

5. The method of claim 1, wherein a controller is configured to compare the concentration with a fuel additive specification, and to control the flow control device to increase flow through to the fuel additive dispenser when the concentration is less than the specification.

6. The method of claim 1, wherein the fuel line, the fuel additive sensor, the fuel additive dispenser and the at least one flow control device are within the fuel tank of the vehicle.

7. The method of claim 6, wherein the vehicle is an aircraft.

* * * * *